US012643923B2

(12) United States Patent (10) Patent No.: US 12,643,923 B2
Rodrigo (45) Date of Patent: Jun. 2, 2026

(54) METHOD OF CLARIFYING A CRUDE PROTEIN SOLUTION

(71) Applicant: Cytiva BioProcess R&D AB, Uppsala (SE)

(72) Inventor: Gustav Rodrigo, Uppsala (SE)

(73) Assignee: Cytiva BioProcess R&D AB, Uppsala (SE)

( * ) Notice: Subject to any disclaimer, the term of this patent is extended or adjusted under 35 U.S.C. 154(b) by 394 days.

(21) Appl. No.: 18/549,552

(22) PCT Filed: Apr. 11, 2022

(86) PCT No.: PCT/EP2022/059593
§ 371 (c)(1),
(2) Date: Sep. 7, 2023

(87) PCT Pub. No.: WO2022/223344
PCT Pub. Date: Oct. 27, 2022

(65) Prior Publication Data
US 2024/0294568 A1 Sep. 5, 2024

(30) Foreign Application Priority Data

Apr. 19, 2021 (GB) ..................................... 2105559

(51) Int. Cl.
*C07K 1/36* (2006.01)
(52) U.S. Cl.
CPC ..................................... *C07K 1/36* (2013.01)
(58) Field of Classification Search
CPC ..................................................... C07K 1/36
See application file for complete search history.

(56) References Cited

FOREIGN PATENT DOCUMENTS

| | | |
|---|---|---|
| CN | 112301006 A | 2/2021 |
| EP | 3754012 A1 | 12/2020 |
| WO | 2007035283 A1 | 3/2007 |
| WO | 2020/229447 A1 | 11/2020 |

OTHER PUBLICATIONS

PCT International Search Report and Written Opinion for PCT/EP2022/059593, mailed, Sep. 19, 2022 (13 pages).
GB Combined Search Report and Examination Report for GB2105559.5, mailed Dec. 31, 2021 (3 pages).
Anonymous author: "Optimization of Contaminant Flocculation in Antibody Feed By Calcium Phosphate", Jan. 21, 2009 (Jan. 21, 2009), XP055870879, IP.com Prior Art Database [retrieved on Dec. 9, 2021].
Ip.com Prior Art Database, 2009, Anonymous Author, "Optimization of contaminant flocculation in antibody feed by calcium phosphate" URL: https://priorart.ip.com/IPCOM/000178290/Optimization-of-contaminant-flocculation-in-antibody-feed-by-calcium-phospate paragraph [03.2]; table 3.
First Office Action in corresponding JP application No. 2023-564017, dated Mar. 31, 2026 (4 pages).
Gagnon, et al. "A Ceramic Hydroxyapatite-Based Purification Platform", BioProcess International, 2010, 4(2), LIT#RP0033, pp. 1-8, <URL:https://www.bio-rad.com/webroot/web/pdf/ps/literature/Bulletin_RP0033.pdf>.

*Primary Examiner* — Amber D Steele
(74) *Attorney, Agent, or Firm* — Eversheds-Sutherland (US) LLP

(57) ABSTRACT

Method of clarifying a crude protein solution, the method comprising to provide (100) a volume of the crude protein solution, mixing (101) $Na_2HPO_4$ and $CaCl_2$) in water, forming a first solution, adding (102) the first solution to the volume of crude protein solution, thereby forming a second solution. NaCl is added to the first solution, the crude protein solution and/or to the second solution. The second solution is mixed (103). The thus formed flocculated material is separated (104) from the second solution, obtaining a clarified protein solution. The clarified protein solution may thereafter be purified by chromatography.

7 Claims, 6 Drawing Sheets

METHOD OF CLARIFYING A CRUDE PROTEIN SOLUTION

CROSS REFERENCE TO RELATED APPLICATIONS

This application claims the priority benefit of PCT/EP2022/059593, filed Apr. 11, 2022, which claims the priority benefit to GB Application No. 2105559.5, filed Apr. 19, 2021, the entire contents of which are incorporated herein by reference.

TECHNICAL FIELD

The present disclosure is related to a method of clarifying a crude protein solution, and to a method of purifying proteins from the clarified crude protein solution by chromatography.

BACKGROUND ART

Purification of proteins such as for example antibodies and monoclonal antibodies, mAbs, from a crude protein solution obtained through harvest from a cell culture used for producing the protein of interest normally requires the use of a combination of different filtration steps, with or without a preceding centrifugation step.

Convection-based chromatography support materials such as a fibrous substrate, which may for instance be based on electrospun cellulose fibers, e.g. HiTrap Fibro PrismA units from Cytiva, enables the combination of high flow rates with high binding capacity and are, hence, of interest for use in for example mAb purification. If the mAb solution is not well-enough clarified, i.e due to presence of impurities such as e.g. lipids/lipoproteins and/or DNA, when added to the fibrous substrate, the fibrous substrate may only be used for a limited number of cycles due to a significant pressure increase.

There is, hence, a need for clarification methods, such that the lifetime of a support material used for purifying the protein can be increased.

One way of clarifying a crude monoclonal antibody solution is discussed in IP.com number IPCOM000178290D. In this disclosure calcium chloride and sodium phosphate is mixed in water to form a hydroxy-apatite crystal slurry, which is mixed with the antibody solution. The mixture is agitated, followed by centrifugation and flocculated/precipitated cells and submicron particles are removed from the solution, leaving a clarified antibody solution.

For chromatography applications using a convection-based chromatography support materials such as a fibrous substrate, a protein solution clarification method especially developed for this use could be useful.

SUMMARY OF THE INVENTION

It is an object of the present disclosure to provide a method of clarifying a crude protein solution, and a method of purifying proteins from the clarified protein solution using chromatography, wherein the chromatography support material may be a convection-based chromatography matrix such as a fibrous substrate.

The invention is defined by the appended independent claims. Non-limiting embodiments emerge from the dependent claims, the appended drawings and the following description.

According to a first aspect there is provided a method of clarifying a crude protein solution. The method comprises to provide a volume of the crude protein solution; mixing $Na_2HPO_4$ and $CaCl_2$) in water, forming a first solution, and to add the first solution to the volume of the crude protein solution, thereby forming a second solution. NaCl is added to the first solution, the crude protein solution and/or to the second solution. Thereafter the second solution is mixed and the thus formed flocculated material is separated from the second solution, obtaining a clarified protein solution.

The crude protein solution may comprise proteins such as antibodies, monoclonal antibodies, insulin or any kind of protein of interest. The crude protein solution may be obtained through harvest from a cell culture (such as from a mammalian, yeast, plant, bacteria or insect cell line) used for producing the protein of interest. The crude protein solution may comprise, apart from the protein of interest, one or more impurities, such as cells, cell parts, host cell proteins, DNA and submicron particles such as lipids and lipoproteins. The protein solution may, alternatively, not contain any cells.

In the first solution $Na_2HPO_4$ and $CaCl_2$) forms hydroxy-apatite crystals. The NaCl added in the first solution is believed to hinder the proteins to bind to the formed crystals. The skilled person is aware that NaCl is a natural elution agent for proteins from hydroxyapatite.

After mixing of the second solution, impurity components present in the protein solution, such as for example cells, cell parts and submicron particles such as lipids and lipoproteins together with the formed crystals form flocculated material.

The separation of the flocculated material from the second solution can be obtained by centrifugation, wherein the protein is present in the formed supernatant.

The clarified protein solution has a low particle content as the amount of lipids, lipoproteins and/or DNA in the solution has been reduced. Further, the method may result in a high protein yield.

The clarified protein solution may then be purified using for example a HiTrap Fibro unit from Cytiva. The fiber/membrane unit may be used for a repeated number of cycles without a significant pressure increase compared to when protein solutions not clarified the same way are purified with such fiber/membrane units.

The concentration of NaCl in the second solution may be 0.2-1.0 mol/L, the concentration of $PO_4^{2-}$ may be 0.01-0.1 mol/L, and the concentration of $Ca^{2+}$ may be 0.01-0.1 mol/L, wherein the molar proportion of NaCl to $PO_4^{2-}$ may be 2:1 to 100:1, and the molar proportion of $Ca^{2+}$ to $PO_4^{2-}$ may be 1:10 to 10:1. All said concentrations and said proportions are calculated based on the addition of NaCl, $Na_2HPO_4$ and $CaCl_2$) to the crude protein solution.

The concentrations and proportions of NaCl, $Na_2HPO_4$ and $CaCl_2$) mentioned above do not take into account the possible presence of these ions in the original crude protein solution.

The volume of the crude protein solution constitutes 50-95% of a volume of the second solution, thereby there is a dilution of the protein solution in the second solution.

The optimal concentration and proportion of the different salts added to the crude protein solution may depend on the specific crude protein solution, i.e. how much cells (if any) and cell components there are in the solution and the clarification requirements of the resulting protein solution.

In one specific example, the second solution comprised 20 mM $CaCl_2$), 50 mM $Na_2HPO_4$ and 600 mM NaCl.

The second solution may be mixed for at least 10 minutes.

The solution may be mixed using e.g. vortex. The mixing time may be at least 10 minutes, at least 30 minutes, at least 60 minutes or at least 90 minutes. The mixing may also comprise an end-over-end mixing.

The flocculation occurs more or less instantaneously, but the degree of flocculation and adsorption of molecules to the hydroxyapatite can be increased by increasing the reaction time in the second solution, such as by end-over-end mixing.

According to a second aspect there is provided a method of purifying a protein by chromatography. The method comprises to provide a chromatography support material provided with ligands having binding affinity for the protein, providing a clarified protein solution obtained according to the method described above, and adding the clarified protein solution to the chromatography support material allowing the ligands to capture the protein. Thereafter, the chromatography support material is washed, the protein eluted from the chromatography support material, and the thus formed eluate containing the protein collected.

The choice of ligand depends on the protein to be purified. Some examples are protein A, protein G, protein L, specific antibodies binding the protein of interest, etc.

By adding a clarified protein solution, clarified as described in the method above, the chromatography support material may be reused a plurality of times, and for some set-ups and conditions more than 100 times, without any major clogging issues or significant pressure increase.

The chromatography support material may be a diffusion-based matrix. The chromatography support material may have an effective pore size of 0.01-2.0 μm. An example of a diffusion-based matrix is an agarose-based chromatography support material.

The chromatography support material could comprise a convection-based chromatography matrix. Said convection-based chromatography matrix may be a fibrous substrate. Said fibrous substrate may be based on electrospun polymeric fibers or cellulose fibers, optionally non-woven fibers. The fibrous substrate may thus be a fibrous non-woven polymer matrix. The fibers comprised in said fibrous substrate have a cross-sectional diameter of 10-1000 nm, such as 200-800 nm, 200-400 nm or 300-400 nm. Such a fibrous substrate can be found in a HiTrap Fibro unit from Cytiva.

The clarified protein solution may be centrifuged and/or filtered before added to the chromatography support material.

The clarified protein solution may be centrifuged and/or filtered such as to remove any remaining solid particles form the protein solution.

BRIEF DESCRIPTION OF THE DRAWINGS OF THE DRAWINGS

Figure 4:
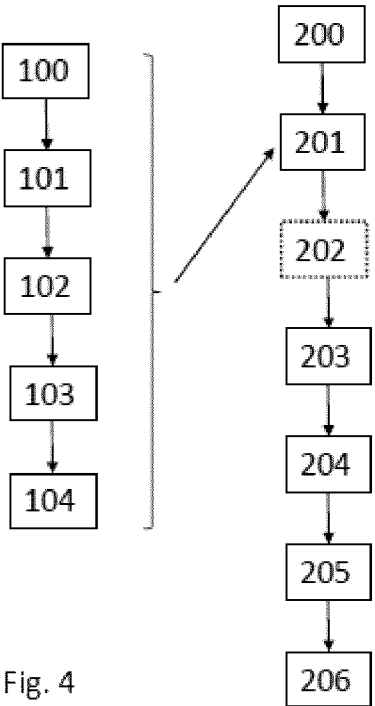

FIG. 4 schematically illustrates a method of clarifying a crude protein solution and a method of purifying the protein from such obtained clarified protein solution by chromatography.

DETAILED DESCRIPTION

Purification of proteins, such as antibodies and monoclonal antibodies, mAbs, from a crude protein solution obtained through harvest from a cell culture used for producing the protein of interest, normally requires the use of a combination of different filtration steps, with or without a preceding centrifugation step. The crude protein solution may comprise, apart from the protein of interest, one or more impurities such as cells, cell parts, host cell proteins, DNA and submicron particles such as lipids and lipoproteins. The protein solution may, alternatively, not contain any cells.

Below is described a protein solution clarification method, illustrated in FIG. 4. When such a clarified protein solution is purified by chromatography, problems with chromatography support material clogging and pressure increase may be reduced. Thereby the lifetime of a convection-based chromatography matrix such as a fibrous substrate, used for purifying the protein can be increased. The clarified protein solution has a lowered opacity compared to the crude protein solution, as the amount of lipids, lipoproteins, cells, cell parts and/or DNA in the solution has been reduced. Further, the method may result in a high protein yield.

Such a clarified protein solution may be purified, FIG. 4, using for example a HiTrap Fibro unit from Cytiva comprising a fibrous substrate. Such a chromatography support material may be based on electrospun cellulose fibers, and enables the combination of high flow rates with high binding capacity and is, hence, of interest for use in protein purification. These units are sensitive to particles since these might block the pores between the fibers and lead to an increase in back-pressure. Particles (even sub-micron particles) present in the mAb protein solution typically lead to an opacity, even after filtering with a 0.2 μm filter. Hence, opacity might be seen as a measure of "content of particulate material". If a protein solution is too opaque when added to the fibrous substrate, the fibrous substrate may only be used for a limited number of cycles due to a significant pressure increase.

The clarification method described below provides a solution to this problem. By adding a clarified protein solution to the chromatography support material, the support material may be reused a plurality of times, and for some set-ups and conditions more than 100 times, without any clogging issues or significant pressure increase.

In one embodiment of the method, NaCl, $Na_2HPO_4$ and $CaCl_2$) are mixed 101 in water to form a first solution. $Na_2HPO_4$ and $CaCl_2$) form hydroxyapatite crystals in the solution. The first solution is added 102 to a provided 100 volume of the crude protein solution, forming a second solution which is mixed 103. After mixing of the second solution for at least 10 minutes, impurity components present in the protein solution, such as for example cells, cell debris and submicron particles such as lipids and lipoproteins together with the formed crystals form flocculated material. The presence of NaCl, a common elution agent in hydroxy apatite chromatography, prevents the proteins from binding to the formed crystals and, thus, increases the yield in the clarification step. As an alternative, or in addition, to adding NaCl to the first solution, the NaCl may be added directly to the crude protein solution and/or directly to the second solution. Next the thus formed flocculated material is separated 104 from the second solution, obtaining a clarified protein solution.

The concentration of NaCl in the second solution may be 0.2-1.0 mol/L, the concentration of $PO_4^{2-}$ may be 0.01-0.1 mol/L, and the concentration of $Ca^{2+}$ may be 0.01-0.1 mol/L, wherein the molar proportion of NaCl to $PO_4^{2-}$ may be 2:1 to 100:1, and the molar proportion of $Ca^{2+}$ to $PO_4^{2-}$ may be 1:10 to 10:1. All said concentrations and said proportions are calculated based on the addition of NaCl, $Na_2HPO_4$ and $CaCl_2$) to the crude protein solution. Any salts or components already present in the crude protein solution, such as in a culture medium or in an original feed, are not included in the concentration calculations herein. Thus, the concentrations and proportions mentioned are only based on the components added according to the method disclosed herein.

The volume of the crude monoclonal antibody feed may constitute 50-95% of a volume of the second solution, thereby there is a dilution of the protein in the second solution.

The optimal concentration and proportion of the different salts added to the crude protein solution may depend on the specific crude protein solution, i.e. how much cells and cell components there are in the solution and the yield and opacity requirements of the clarified protein solution and the nature of the protein itself.

NaCl, $Na_2HPO_4$ and $CaCl_2$) may be mixed 101 in water by diluting all salt components in the same water volume during stirring or vortex. Alternatively, one or more salt components may be first diluted in a volume of water before being mixed with the other salt components.

The flocculation occurs more or less instantaneously, but the degree of flocculation can be increased by increasing the reaction time such as by end-over-end mixing during or after the mixing 103 of the second solution.

After mixing the salt components with the crude protein solution, impurities such as cells, cell parts and/or submicron particles such as lipids and lipoproteins together with the formed crystals form flocculated material, which may be separated 104 from the solution by centrifugation and/or depth filtration step(s). Thereby a clarified protein solution is obtained in the formed supernatant, the supernatant with proteins being less opaque than the crude protein solution.

The obtained 201 clarified protein solution may be added 203 to a provided 200 chromatography support material provided with ligands having binding affinity for the protein, such as Protein A, Protein L, Protein G or any other antibody-binding affinity ligand. Thereafter, the support material is washed 204, and the protein captured to the ligands in the chromatography support material is then eluted 205 and the eluate comprising the protein collected 206. Purification of proteins from using such a clarified protein solution reduces problems with pressure increase over the chromatography support material, thereby increasing the lifetime of a support material, which support material could be for example a convection-based chromatography matrix such as a fibrous substrate, as compared to non-clarified protein solutions. Alternatively, the clarified protein solution may also be centrifuged and filtered 202 before added 203 to the chromatography support material.

In the following is described specific examples of the method. It is also discussed how to optimise a concentration of salt components such as to obtain a low particle content and a high protein yield.

EXPERIMENTAL

Experiment 1—Clarifying Crude Protein Solution

Flocculation

Figure 1A:
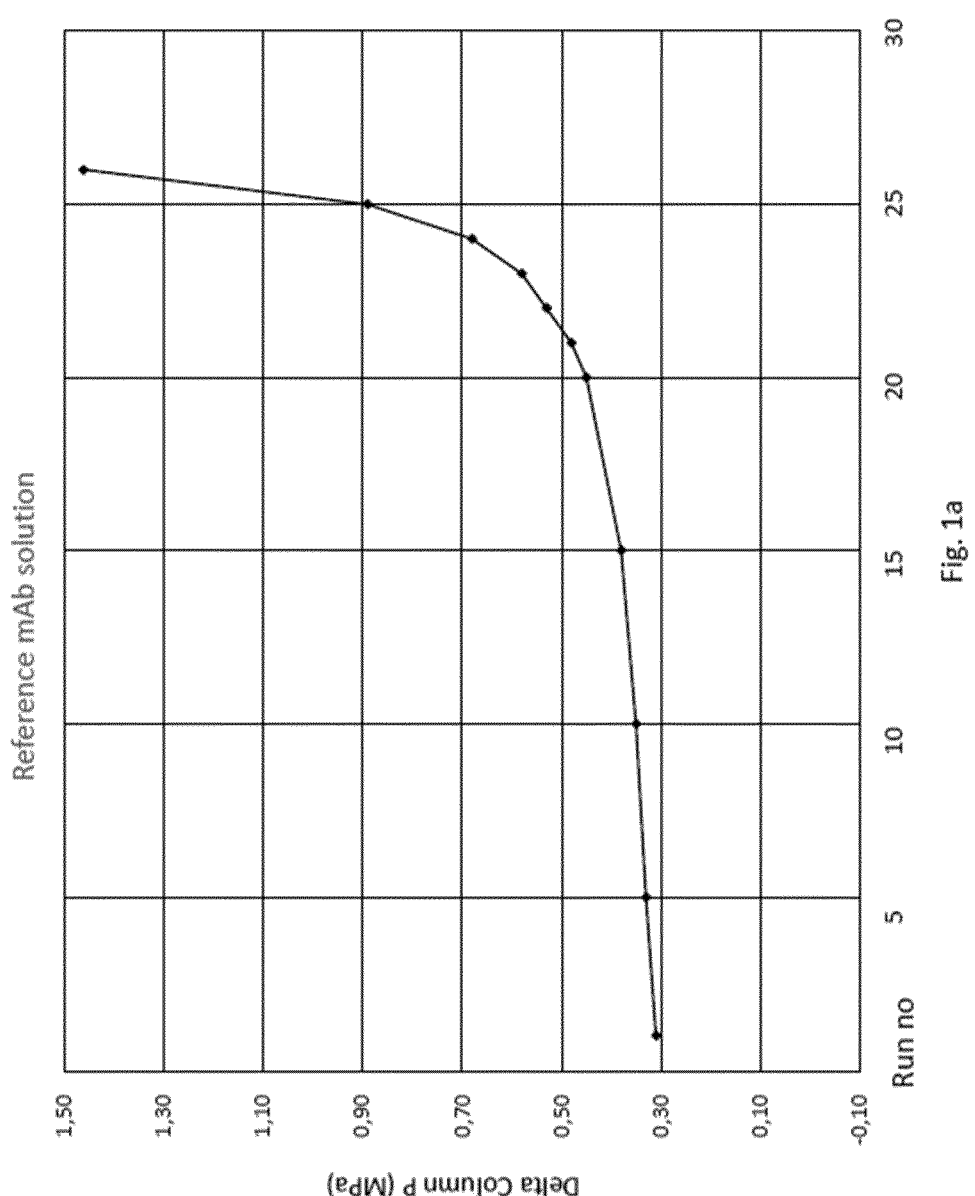
FIGS. 1a and 1b are graphs illustrating the number of cycles a specific chromatography support material can be reused without clogging/significant pressure increase when used for purifying a crude monoclonal antibody solution without any pre-treatment of the monoclonal antibody solution and with a pre-flocculation treatment, respectively.
Figure 1B:
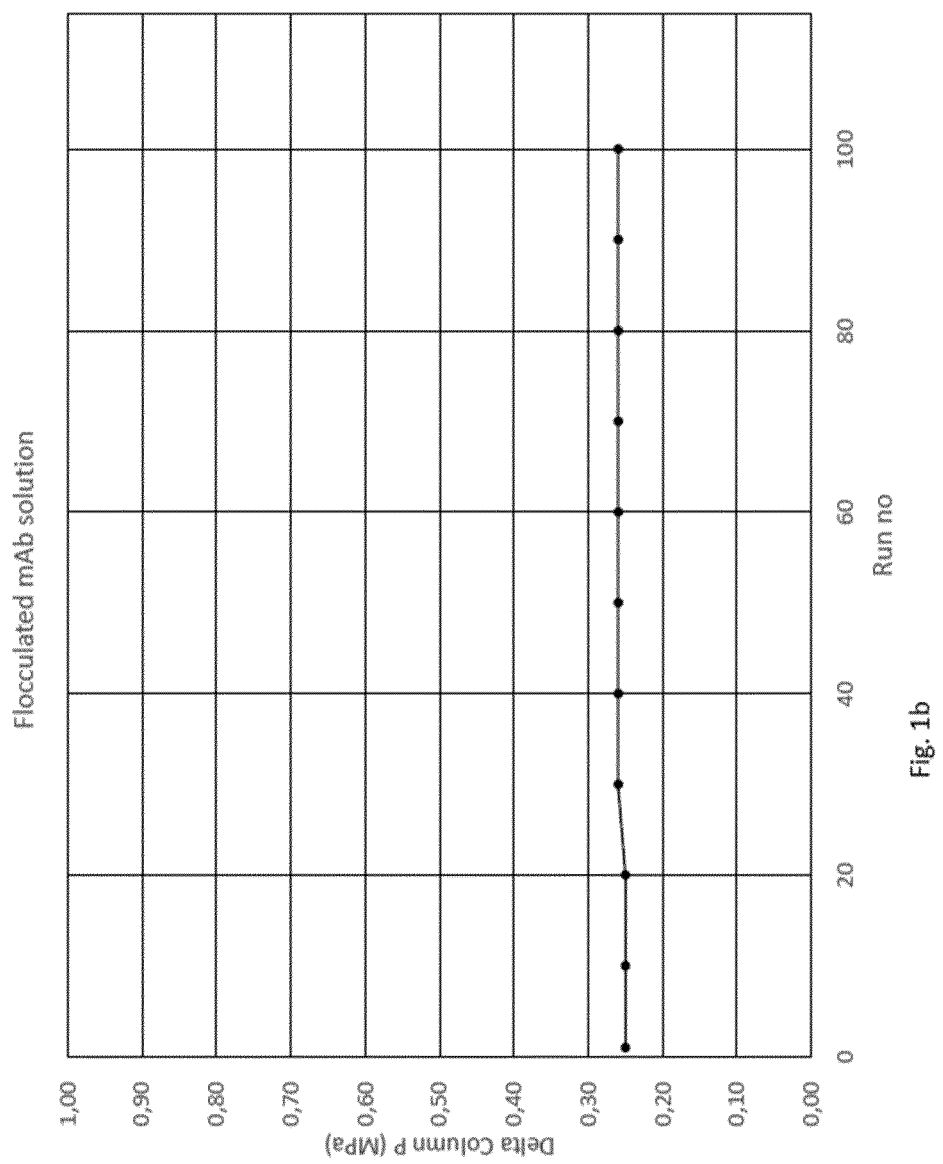
Figure 2:
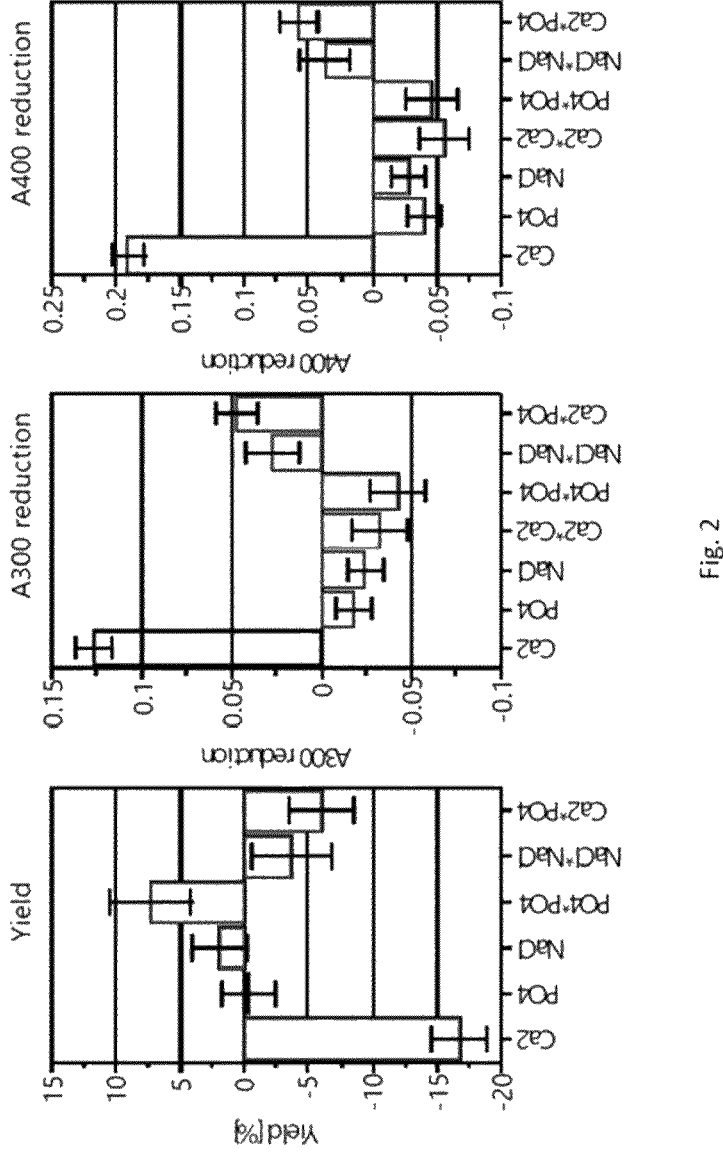
FIG. 2 shows three graphs modelling the positive/negative influence of the concentrations of NaCl, $CaCl_2$), and $Na_2HPO_4$ on yield and on opacity, measured as reduction in absorbance at 300 nm (A300) and reduction in absorbance at 400 nm (A400), in a clarified monoclonal antibody.
Figure 3A:
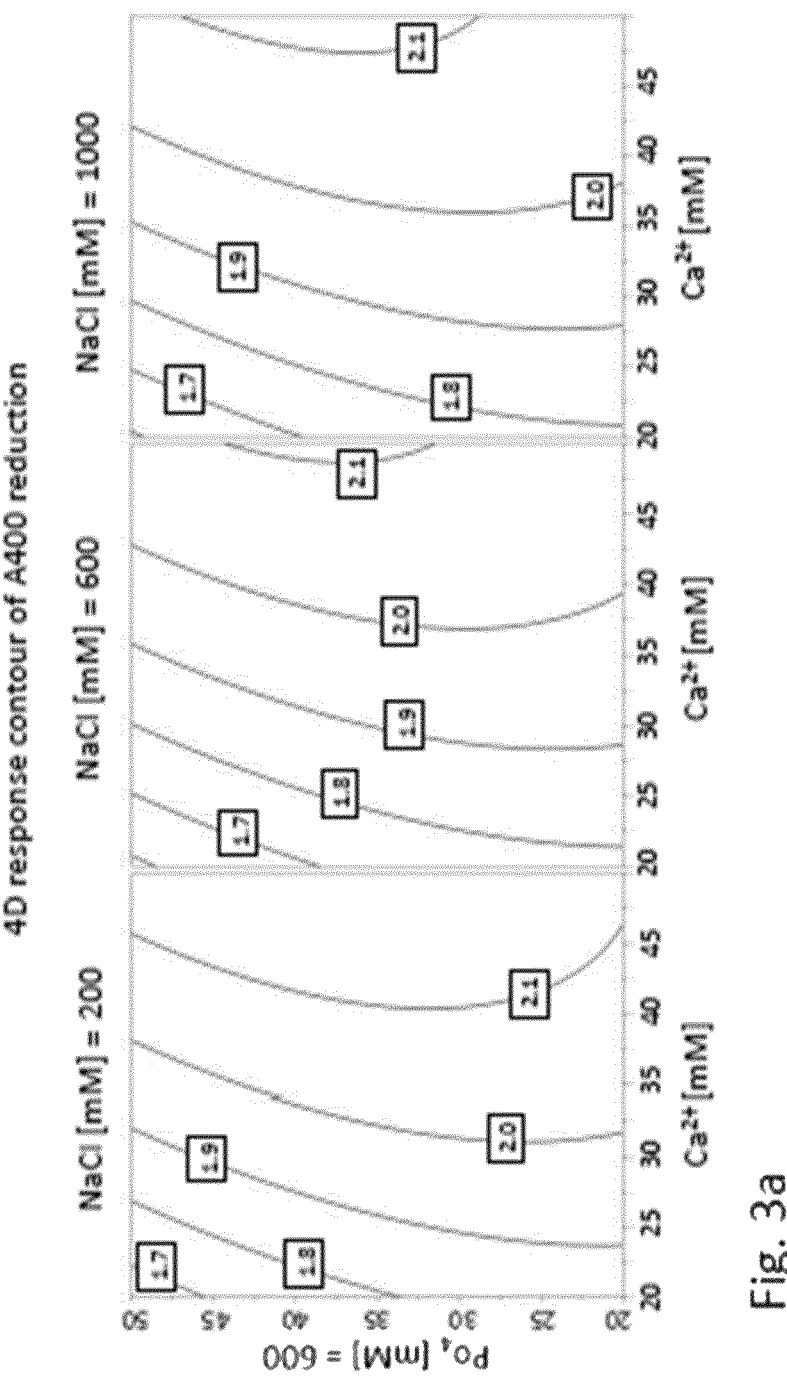
FIGS. 3a and 3b illustrate the model's response contour of yield and absorbance reduction of a clarified crude mAb solution compared to a crude, non-clarified, mAb solution measured at 400 nm (A400) for different concentrations of three added salts in a clarified mAb solution.
Figure 3B:
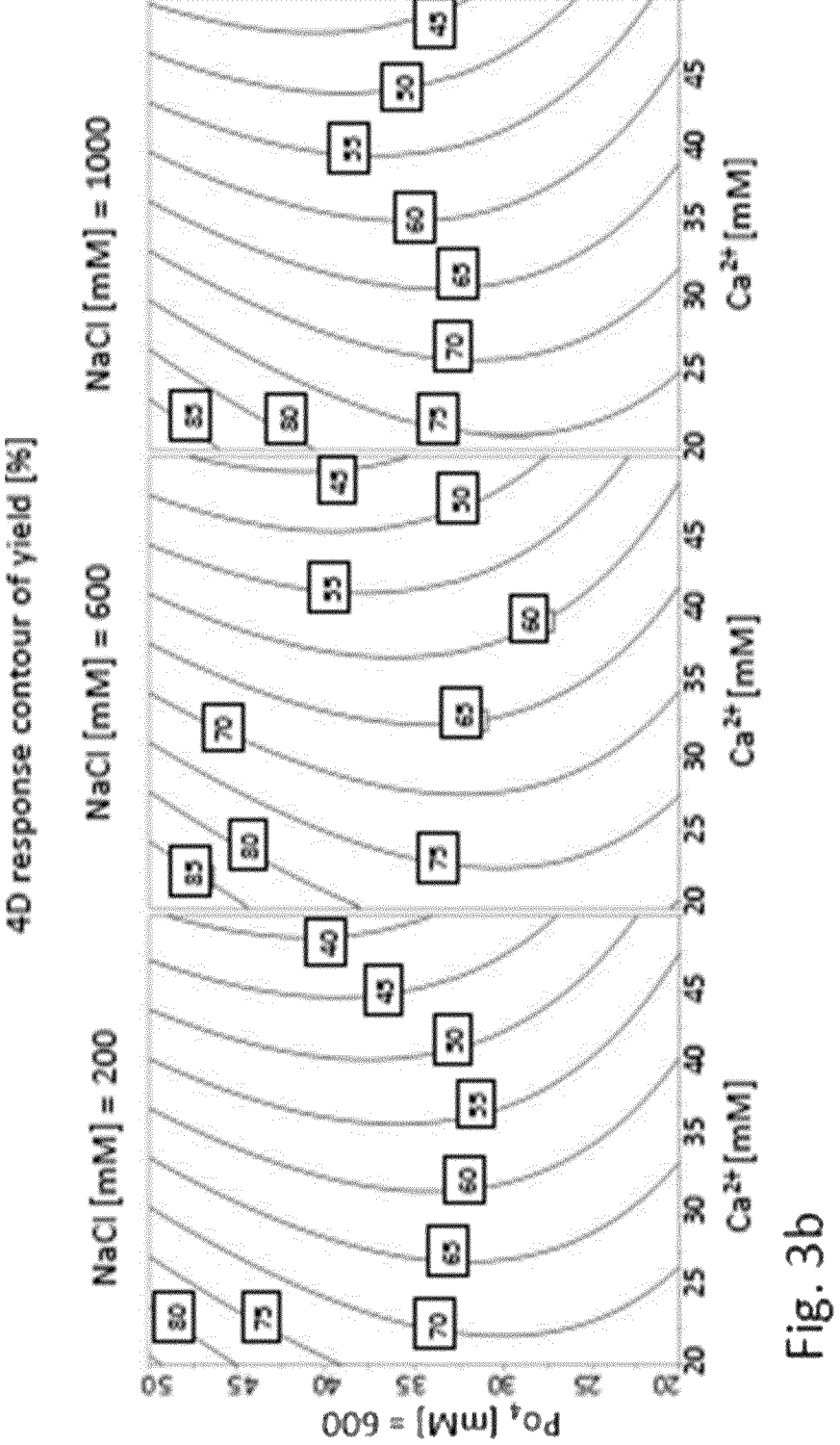

As is shown in the model plots in FIGS. 2 and 3a, 3b, when clarifying a crude protein solution (without cells), here exemplified with a crude monoclonal antibody, mAb solution, by adding NaCl, $CaCl_2$), and $Na_2HPO_4$ to the crude mAb solution, a high yield and a high purity (high absorbance reduction, opacity/particle reduction) of the mAb solution do not match. A trade-off has to be done between yield and purity. In FIG. 2 is shown three graphs and the positive/negative influence of the concentration of NaCl, $CaCl_2$), and $Na_2HPO_4$ on yield and on opacity, measured as a reduction in absorbance compared to the crude mAb solution at 300 nm (A300) and at 400 nm (A400), in the model obtained for clarifying the mAb solution. In FIGS. 3a and 3b is illustrated the response contour of yield and absorbance reduction of a clarified mAb solution compared to a crude mAb solution measured at 400 nm (A400) for different concentrations of the three added salts in the model for clarification of the crude mAb solution. The supernatant mAb yield was evaluated by running a MabSelect SuRe column (HiTrap 1 mL), integrating the elution peak (data not shown) and comparing it to the reference (non-flocculated) peak as a percentage value.

To verify these models, flocculation experiments were performed on a crude mAb solution. The flocculation experiments were performed at a setting supposedly giving a high yield (not necessarily the optimum).

In the verification experiment 760 ml of the crude mAb solution from a monoclonal antibody harvest was flocculated, according to the settings for high yield, as follows. Volumes of 20 mL $CaCl_2$) (1000 mM), 100 mL $Na_2HPO_4$ (500 mM) and 120 mL NaCl (1000 mM) were mixed and vortexed thoroughly at room temperature. The crude mAb solution (760 mL) was then added. The concentration of the salt components in the formed solution was then 20 mM calcium, 50 mM phosphate and 600 mM NaCl, as calculated only based on the above-mentioned addition.

The solution was incubated and allowed to react for at least 60 minutes with slow stirring at room temperature (RT). Thereafter the solution was centrifuged (3200×g) for minutes at RT. The supernatant was collected and then filtered through a Sterivex 0.2 μm filter (MerckMillipore) using ÄKTA explorer 100 system, flow rate 50 mL/min. There was an observed low pressure increase (0.6 bar to 1.2 bar), but one Sterivex unit could be used to filter the about 900 mL of solution.

As a control sample, a crude mAb solution was mixed with buffer (20 mM Tris-HCl, 150 mM NaCl, pH 7.5), such that the dilution of the control sample was the same as the dilution of the flocculated sample.

The absorbance reduction factors and yield were calculated and evaluated. The specific experiment resulted in a yield of 86.0% and an A400 reduction of 1.643.

Chromatography

A mAb solution treated as described above, and an untreated (but equally diluted) crude reference mAb solution were applied to a chromatography support material being a fibrous non-woven polymer matrix, a HiTrap Fibro unit, using an ÄKTA pure chromatography system, Cytiva.

Stock solutions used were 2 M NaCl, 0.25 M $NaH_2PO_4xH_2O$, 0.25 $Na_2HPO_4x2H_2O$, 0.25 M $NaOAcx3H_2O$ and 0.25 M HOAc. All stock solutions, except 0.25 M HOAC, were filtered with water suction device and Nalgene 1000 mL Rapid-Flow Filter unit 0.1 μm aPES membrane 90 mm diameter.

Chromatography buffers and solutions for the different chromatography steps used were: Equilibration/Wash1 buffer: 20 mM Na-phosphate, 500 mM NaCl, ~pH 7 with pH dipstick, conductivity ca 43 mS/cm. Wash2 buffer: 50 mM Na—OAc, ~PH 5.5, cond ca 3 mS/cm. Elution buffer: 100 mM Na-acetate, target pH 3.5. Measured ~pH 3.5 with pH dipstick, conductivity ca 0.5 mS/cm. CIP (cleaning in place) solution: 0.5 M NaOH from Titrisol ampoules. Titrisol 1 M ampoule, approx 116 mL+1884 g (=mL) $H_2O$=2 L, 0.5 M NaOH. Conductivity ca 100 mS/cm.

The HiTrap Fibro unit was a PrismA unit provided with protein A as immobilised ligand in the chromatographic medium. The membrane volume (MV) was 0.4 mL. The capacity was not measured, instead an estimated QB10% (capacity at 10% breakthrough) of 31 mg/ml, corresponding to a load of 0.8×31=24.8=25 mg/mL, corresponding to 0.4×25=10 mg of mAb, was used for estimating the sample volume.

The mAb solution samples were prepared as above and also contained 0.02% Na-azide. The estimated mAb concentration was 1.45 mg/mL. The Na-azid addition does not contribute to the clarification but acts as a preservative to prevent microbial growth.

The reference, diluted mAb solution with Na-azide was mixed with 240 ml of 20 mM Tris-HCl, 150 mM NaCl, pH 7.5. This dilution corresponded to the dilution of the clarified sample. After dilution estimated concentration of mAb was 0.76×2.26=1.7 mg/mL. The mix was filtered through 0.2 μm Sterivex cylinder filters (MerckMillipore) using ÄKTA explorer 100 system, flow rate 50 mL/min, max pressure 3 bar. A pressure increase was observed and four Sterivex units were needed to filter the about 1000 ml of reference solution.

A HiTrap Fibro unit, in an ÄKTA pure 150 system was used. The ÄKTA pure 150 system was primed with buffers. The method and the units were tested in blank runs with water in sample inlet. The estimated load was approximately 25 mg/mL, corresponding to 10 mg mAb (see above). Estimated sample mAb concentration was 1.7 mg/mL, 10/1.7=5.9=6 mL sample volume in the scouting runs.

With the reference sample, i.e. not pre-treated mAb solution, the cycling test was stopped in cycle 26, because of a high pressure, while 100 cycles were performed with the mAb solution pre-treated as described above without any major pressure increase. This clearly indicates that the clarification method, flocculation, as a technique can be useful for problematic mAb feeds, i.e. protein solutions comprising cells and cell parts. The mAb yields were comparable, 85% with the reference mAb solution (26 cycles), and 89% with the flocculated solution (100 cycles). The average eluate volumes were approximately 2 mL, corresponding to 5 MV, which is in the normal range for Fibro HiTrap units. The reference mAb solution was diluted with buffer to match the dilution of the flocculated mAb solution. In spite of this, the host cell protein (HCP) concentration was clearly lower in the flocculated mAb solution (182035 ng/ml), compared to the reference, diluted mAb solution (269239 ng/ml). This corresponds to approximately 32% reduction (182035/269239=0.68) in HCP with flocculation in this case. This indicated that the flocculation precipitate consists at least partly of HCP. Interestingly, the reduction in HCP level in the eluate was even larger measured as ppm, approximately 62%(324/861=0.38). The protein A (immobilised ligand) leakage was higher in the reference mAb solution, 1.8 ppm, compared to the flocculated mAb solution, 0.3 ppm. This could reflect the higher ligand leakage in the initial cycles, since the scouting with reference mAb solution stopped at 26 cycles, compared to 100 cycles for the flocculated mAb solution. Without being bound to any theory, this may be an effect of the lower HCP level, but to our knowledge this has not been observed before. The conclusion is that flocculation definitely is a technique that could be useful for preparing crude protein solutions for chromatography, for example when using a convection-based chromatography matrix such as a fibrous substrate, for example a fibrous non-woven polymer matrix such as the one found in a HiTrap Fibro unit from Cytiva, thereby, enabling more cycles without clogging the units. Furthermore, flocculation seems to reduce the amount of HCP, and perhaps also protein A leakage, in the eluate.

The clarification described above/flocculation is a powerful complement to depth filtration for removal of opacity from mAb samples. High yield and purity was obtained in this study after the chromatographic step.

Experiment 2—Clarifying Crude Protein Solution Comprising Cells

Flocculation

A mixture of 180 ml of 500 mM $Na_2HPO_4$, 180 ml of 5000 mM NaCl and 45 ml of 2000 mM $CaCl_2$ was prepared and added to 1095 ml of a crude mAb cell culture comprising cells. The mAb titre of the mAb cell culture before dilution was 3.80 mg/ml, and the initial amount of mAb was 4161 mg mAb in this mixture. (Final concentration of flocculation components: 60 mmol $CaCl_2$, 60 mmol $Na_2HPO_4$, 600 mmol NaCl, as calculated only based on the above-mentioned addition.)

The cell culture with hydroxyapatite was stirred for 2 h and then centrifuged to remove hydroxyapatite and cells. The supernatant was collected and filtered through a 0.2 μm ULTA HC filter (Cytiva®).

The mAb yield in the harvest/flocculation step was determined to 94%. The turbidity of the supernatant before and after 0.2 μm filtration was 21.5 and 2.6 FNU (Formazin Nephelometric Unit), respectively.

Chromatography

The flocculated mAb cell culture supernatant was 0.2 μm filtered just prior to loading to a HiTrap Fibro PrismA unit (matrix volume 0.4 mL). The turbidity after the filtration was 2.01 FNU.

The sample load in each Fibro PrismA cycle was 80% of the dynamic binding capacity at 10% breakthrough (QB10%). The QB10% value was 30 mg/mL so the sample load was 24 mg/mL. The mAb concentration in the start sample was 2.67 mg/ml, thus the volume loaded was 3.6 mL.

All buffers but the elution buffer were applied with the same pump.

In the chromatography method the following parameters and steps were used:

Flow rate: 16 ml/min except for CIP (8 ml/min)

Equilibration: 2 ml Equilibration buffer (A1: 50 mM $NaPO_4$+150 mM NaCl, pH 7.4)

Sample: 3.6 ml of mAb sample (S1)

Wash 1: 6 ml wash 1 buffer (A2: 20 mM NaPO4+500 mM NaCl, pH 7.0)

Wash 2: 6 ml wash 2 buffer (A3: 50 mM NaOAc, pH 5.5)

Elution: 7 ml Elution buffer (B1: 100 mM NaOAc, pH 3.5)

CIP: 10 ml of 0.5 M NaOH (A4: 2 ml at 16 ml/min and 8 ml at 8 ml/min) and 4 ml of equilibration buffer A1 at 8 ml/min Re-equilibration: 4 ml equilibration buffer (A1: 50 mM NaPO4+150 mM NaCl, pH 7.4) at 16 ml/min The eluates from the 200 cycles were collected in a common bulk. The mAb yield was 94.5% over the Fibro PrismA step. The turbidity in the eluate was <1 FNU. HCP in the start material applied to Fibro PrismA was 270323 ppm which was reduced to 253 ppm after the Fibro PrismA step. The PrismA ligand leakage was <1 ppm.

From this experiment it was shown that the fiber/membrane unit could be used for a repeated number of cycles, 200 cycles, with a pressure increase of only 25%. The flocculation step of the crude mAb solution comprising cells reduced the turbidity drastically making it possible to run 200 cycles.

The invention claimed is:

1. Method of clarifying a crude protein solution, the method comprising:
   providing a volume of the crude protein solution;
   mixing $Na_2HPO_4$ and $CaCl_2$ in water, forming a first solution;
   adding the first solution to the volume of crude protein solution, thereby forming a second solution;
   wherein NaCl is added to the first solution, the crude protein solution and/or to the second solution;
   mixing the second solution;
   separating thus formed flocculated material from the second solution, obtaining a clarified protein solution.

2. The method of claim 1, wherein the concentration of NaCl in the second solution is 0.2-1.0 mol/L, the concentration of $PO_4^{2-}$ is 0.01-0.1 mol/L, and the concentration of $Ca^{2+}$ is 0.01-0.1 mol/L, wherein the molar proportion of NaCl to $PO_4^{2-}$ is 2:1 to 100:1 and the molar proportion of $Ca^{2+}$ to $PO_4^{2-}$ is 1:10 to 10:1, wherein all said concentrations and said proportions are calculated based on the addition of NaCl, $Na_2HPO_4$ and $CaCl_2$ to the crude protein solution.

3. The method of claim 1, wherein the second solution is mixed for at least 10 minutes.

4. Method of purifying a protein by chromatography, the method comprising:
   providing a chromatography support material provided with ligands having binding affinity for the protein,
   providing a clarified protein solution obtained according to the method of claim 1,
   adding the clarified protein solution to the chromatography support material allowing the ligands to capture the protein,
   washing the chromatography support material,
   eluting the protein from the chromatography support material,
   collecting the thus formed eluate containing the protein.

5. The method of claim 4, wherein the chromatography support material is a convection-based chromatography matrix such as a fibrous substrate.

6. The method of claim 5, wherein the fibrous substrate is a fibrous non-woven polymer matrix.

7. The method of claim 4, wherein the clarified protein solution is centrifuged and/or filtered before added to the chromatography support material.

\* \* \* \* \*